United States Patent [19]

Benicewicz et al.

[11] Patent Number: 5,382,665
[45] Date of Patent: Jan. 17, 1995

[54] SYNTHESIS OF OXAZOLINES AND OXAZINES

[75] Inventors: Brian C. Benicewicz; Michael A. Mitchell, both of Los Alamos, N. Mex.

[73] Assignee: The United States of America as represented by the United States Department of Energy, Washington, D.C.

[21] Appl. No.: 32,935
[22] Filed: Mar. 17, 1993
[51] Int. Cl.6 ............................................ C07D 233/06
[52] U.S. Cl. ..................................... 544/88; 544/53; 548/146; 548/239
[58] Field of Search ........................... 544/88; 548/239

[56] References Cited

U.S. PATENT DOCUMENTS 2,579,478 12/1951 Djerassi et al. .
2,844,589 7/1958 Hess ..................... 548/239
2,968,657 1/1961 Perry et al. .
3,331,851 7/1967 Bassiri et al. ......................... 548/239
3,483,141 12/1969 Litt et al. .............................. 548/239
3,562,263 2/1971 Litt et al. .............................. 548/239
3,681,329 8/1972 Litt ...................................... 548/239
4,203,900 5/1980 Kaiser .................................. 548/239
5,034,536 7/1991 Fazio ................................... 548/239

FOREIGN PATENT DOCUMENTS 1103605 2/1968 United Kingdom ................... 544/88

OTHER PUBLICATIONS

Yamawaki et al., "Potassium Fluoride on Alumina. An Efficient Solid Base for Elimination, Addition, and Condensation," Bull. Chem. Soc. Jpn., 56, 1885–1886 (1983).
Ando et al., "Fluoride Salts on Alumina as Reagents for Alkylation of Phenols and Alcohols," Bull. Chem. Soc. Jpn., 55, 2504–2507 (1982).
Clark et al., "Fluoride Ion Catalysed Michael Reactions," Chem. Letters, pp. 1145–1148, (1983).
Ando et al., "Alumina-supported Fluoride Reagents for Organic Synthesis: Optimisation of Reagent Preparation and Elucidation of the Active Species," J. Chem. Soc. Perkin Trans. II, pp. 1133–1139, (1986).
Yamawaki et al., "N-alkylation of Amides and N-Heterocycles with Potassium Fluoride on Alumina," Chem. Letters, pp. 1143–1146, (1981).
Clark et al., "Calcium Fluoride-supported Alkaki Metal Fluorides. New Reagents for Nucleophilic Fluorine Transfer Reactions," J. Chem. Soc., Chem. Commun., pp. 791–794, (1986).
Clark et al., "The Synthesis of 1,4-Diketones via Fluoride-catalysed Michael Addition and Supported-permanganate-promoted Nef Transformation," J. Chem. Soc. Perkin Trans. I, pp. 2253–2258 (1983).
Frump, Chemical Reviews, vol. 71, pp. 483–487 1971.

Primary Examiner—Donald G. Daus
Attorney, Agent, or Firm—Bruce H. Cottrell; William A. Eklund; William R. Moser

[57] ABSTRACT

A process of preparing an oxazoline or oxazine compound of the formula

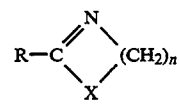

wherein X is an atom selected from the group of oxygen and sulfur, R is selected from the group consisting of $C_{1-10}$ alkyl, $C_{1-10}$ fluoroalkyl, aryl and substituted-aryl, and n is 2 or 3 comprising ring-closing a compound of the formula

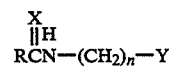

wherein X is an atom selected from the group of oxygen and sulfur, R is selected from the group consisting of $C_{1-10}$ alkyl, $C_{1-10}$ fluoroalkyl, aryl, and substituted aryl, n is 2 or 3, and Y is a bromine or chlorine atom in the presence of a basic reagent consisting essentially of a fluoride salt supported on an inorganic solid substrate is disclosed together with the compounds, 5-bromomethyl-2-phenyl-1,3-oxazoline, 5-methylene-2-phenyl-1,3-oxazine and 4,4-dimethyl-2-vinyl-1,3-oxazoline.

6 Claims, No Drawings

SYNTHESIS OF OXAZOLINES AND OXAZINES

FIELD OF THE INVENTION

The present invention relates to field of organic synthesis and more particularly to the synthesis of oxazolines and oxazines utilizing potassium fluoride coated on an inorganic solid substrate such as alumina.

BACKGROUND OF THE INVENTION 1,3-Oxazoline and 1,3-oxazine compounds have found use in a variety of procedures. Both classes of compounds have been used as monomers in ring opening polymerizations and have been used as protecting groups for carboxyl moieties in organic synthesis. Additionally, chiral oxazolines have proven useful for selected asymmetric syntheses. Also, oxazine and oxazoline derivatives have a variety of biological activities.

Prior syntheses of 1,3-oxazolines and 1,3-oxazines have followed several routes. For example, the reaction between amino alcohols and nitriles is a convenient synthesis, but fails in some instances. Dehydration of $\gamma$-hydroxy amides also a common technique, but requires both harsh conditions and a special experimental setup and procedures. Another important method is ring closure of $\gamma$-halo amides under basic conditions. This procedure usually involves aqueous or alcoholic conditions with the base in high concentration.

Ando et al. have shown that 40% potassium fluoride on neutral alumina is a convenient and efficient reagent for the N-alkylation of amides. However, it does not appear that such a solid supported fluoride reagent has been previously used in an intramolecular ring closure reaction.

In exploring the syntheses of 1,3-oxazolines and 1,3-oxazines, the applicants have now discovered that potassium fluoride on an inorganic solid substrate such as neutral alumina is an effective reagent in converting N-($\beta$-haloalkyl)amides to 1,3-oxazolines and N-($\gamma$-haloalkyl)amides to 1,3-oxazines in an intramolecular ring closing reaction. This discovery has lead to a variety of developments in this area.

Accordingly, it is an object of the present invention to provide a method of synthesizing oxazolines and oxazines using an alkali fluoride, such as potassium fluoride, supported on an inorganic solid substrate such as alumina as a reagent.

It is another object of this invention to provide a method of synthesizing oxazolines and oxazines under relatively mild conditions, i.e., at room temperature using potassium fluoride on an inorganic solid substrate such as alumina as a reagent.

It is still another object of the present invention to provide a method of synthesizing oxazolines and oxazines in high yield using potassium fluoride on alumina as a reagent.

SUMMARY OF THE INVENTION

To achieve the foregoing and other objects, and in accordance with the purposes of the present invention, as embodied and broadly described herein, the present invention provides a process of preparing an oxazoline or oxazine compound of the Formula A

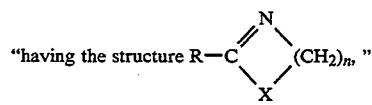

"having the structure $R-C\underset{X}{\overset{N}{\diagup\diagdown}}(CH_2)_n$,"

wherein X is an atom selected from the group of oxygen and sulfur, R is selected from the group consisting of $C_{1-10}$ alkyl, $C_{1-10}$ fluoroalkyl, aryl and substituted-aryl, and n is 2 or 3 comprising ring-closing a compound of the Formula B

"having the structure $\text{RCN(CH}_2)_n-Y$,"

wherein X is an atom selected from the group of oxygen and sulfur, R is selected from the group consisting of $C_{1-10}$ alkyl, $C_{1-10}$ fluoroalkyl, aryl, and substituted aryl, n is 2 or 3, and Y is a bromine or chlorine atom in the presence of a basic reagent consisting essentially of a fluoride salt supported on an inorganic solid substrate.

In another embodiment the present invention provides an improvement in a process of preparing an oxazoline or oxazine compound by ring-closure of one or more precursor materials, the improvement wherein said ring-closure is conducted in the presence of a basic reagent consisting essentially of a fluoride salt supported on an inorganic solid substrate.

The present invention further provides the compounds, 5-bromomethyl-2-phenyl-1,3-oxazoline, 5-methylene-2-phenyl-1,3-oxazine, and 4,4-dimethyl-2-vinyl-1,3-oxazoline and a process of preparing the same.

DETAILED DESCRIPTION

The present invention is concerned with the preparation of oxazolines and oxazines and especially the preparation of 1,3-oxazolines and 1,3-oxazines. In the present process, synthesis of the 1,3-oxazolines and 1,3-oxazines generally begins from precursors of $\gamma$-halo amides or $\beta$-halo amides, although the ring closure reaction may also occur from more than one precursor material. These amide intermediates can be prepared, e.g., by reaction of an acid chloride or anhydride with 2-chloroethyl amine (for oxazolines) or with 3-chloropropyl amine (for oxazines).

The ring closure of the amide precursors to the oxazoline and oxazine products is accomplished with the use of a basic reagent of a fluoride salt supported on an inorganic solid substrate. By use of this reagent, the ring closure can be accomplished under relatively mild conditions and in particular at low temperatures, e.g., at about room or ambient temperature.

The fluoride salt can generally be chosen from among lithium fluoride, sodium fluoride, potassium fluoride, cesium fluoride, and tetra-(lower alkyl)-ammonium fluorides such as tetrabutylammonium fluoride. Potassium fluoride is the preferred fluoride salt.

The inorganic solid substrates upon which the fluoride salt, e.g., potassium fluoride, is coated can be alumina, e.g., basic or neutral alumina, silica gel, magnesium oxide, a molecular sieve such as Linde 4A, a clay such as montmorillonite, or a diatomaceous earth such as that commonly supplied under the tradename Celite. Neutral alumina is preferred as the inorganic solid substrate.

The fluoride salts are generally supported by being coated upon the inorganic solid substrates in amounts of from about 15 percent by weight to about 50 percent by weight based upon the total weight of the fluoride salt and solid substrate, more preferably from about 25 percent by weight to about 40 percent by weight based upon the total weight of the fluoride salt and solid substrate. The fluoride salts can be coated or impregnated on the solid substrates by simple dissolution of the fluoride salts in water, addition of the insoluble solid substrate, and removal of at least the major portion of the water. Materials such as 40 wt % potassium fluoride on alumina, 50 wt % potassium fluoride on Celite TM, and 20 wt % potassium fluoride on silica are available from the Aldrich Chemical Co.

Formula B represents an N-alkylchloride amide, a precursor material, in the present process. In Formula B, X represents an atom selected from the group of oxygen and sulfur, R represents a substituent of a $C_{1-10}$ alkyl, a substituted $C_{1-10}$ alkyl, a $C_{1-10}$ fluoroalkyl, an aryl or a substituted aryl, n is 2 or 3 depending upon whether an oxazoline or oxazine is being prepared, and Y is a halogen atom, preferably a bromine or chlorine atom. The $C_{1-10}$ alkyl can be, e.g., methyl, ethyl, propyl, butyl, pentyl, hexyl, heptyl, octyl, nonyl or decyl, while the $C_{1-10}$ fluoroalkyl is generally a fluorinated or perfluorinated $C_{1-10}$ alkyl. The $C_{1-10}$ alkyl can generally be substituted with halogens, such as chloro, bromo or iodo at one or more positions. The aryl group is generally a phenyl or substituted phenyl, although R may also be any other commonly known aryl group.

Another embodiment of the present invention generally involves the use of a basic reagent consisting essentially of a fluoride salt supported on an inorganic solid substrate to promote ring closure in the general process of preparing oxazoline or oxazine compounds by ring closure of one or more precursor materials. The improvement in this embodiment is the relatively mild processing conditions that can be used when the ring closure is conducted in the presence of the basic reagent consisting essentially of a fluoride salt supported on an inorganic solid substrate.

The present invention is more particularly described in the following examples which are intended as illustrative only, since numerous modifications and variations will be apparent to those skilled in the art.

EXAMPLE A

Various N-alkylchloride amides represented by the foregoing formula of FIG. 2 were prepared from the respective acid chlorides and amides using a Schotten-Baumann procedure.

EXAMPLE 1

Preparation of 2-methyl-1,3-oxazoline was as follows. To 10 milliliters (ml) of tetramethylene sulfone (Sulfolane) was added N-(2-chloroethyl) acetamide (2 grams (g), 16 millimoles (mmole)) and 4 equivalents (10 g) of 40% potassium fluoride on alumina. This mixture was mechanically stirred for about two hours. The product was then distilled at 90° C under a vacuum of 550 mm Hg to give 1.018 g (a yield of about 73 percent).

EXAMPLE 2

Preparation of 2-phenyl-1,3-oxazoline was as follows. N-(2-chloroethyl) benzamide (8 millimoles (mmole)) was mixed with 10 milliliters (ml) of acetonitrile. To this mixture was slowly added 4 equivalents (4.7 g) of 40% potassium fluoride on alumina. This mixture was stirred mechanically until completion of the reaction. Completion of the reaction was followed by thin layer chromatography (TLC) on silica with an ethyl acetate eluent. The potassium fluoride on alumina reagent was filtered off through Celite and the acetonitrile was evaporated. The resulting product was then vacuum distilled with a yield of about 83 percent.

EXAMPLE 3

Preparation of 2-phenyl-1,3-oxazoline was as follows. N-(2-chloroethyl) benzamide (8 millimoles (mmole)) was mixed with 10 milliliters (ml) of acetonitrile. To this mixture was slowly added 4 equivalents (4.7 g) of 40% potassium fluoride on alumina. This mixture was stirred mechanically until completion of the reaction. Completion of the reaction was followed by thin layer chromatography (TLC) on silica with an ethyl acetate eluent. The potassium fluoride on alumina reagent was filtered off through Celite and the acetonirile was evaporated. The resulting product was then vacuum distilled.

EXAMPLE 4

Preparation of 2-nonyl-1,3-oxazoline was as follows. N-(2-chloroethyl) nonylamide (8 millimoles (mmole)) was mixed with 10 milliliters (ml) of acetonitrile. To this mixture was slowly added 4 equivalents (4.7 g) of 40% potassium fluoride on alumina. This mixture was stirred mechanically until completion of the reaction. Completion of the reaction was followed by thin layer chromatography (TLC) on silica with an ethyl acetate eluent. The potassium fluoride on alumina reagent was filtered off through Celite and the acetonitrile was evaporated off. The resulting product was then vacuum distilled with a yield of about 93 percent.

EXAMPLE 5

Preparation of 2-nonyl-1,3-oxazine was as follows. N-(2-chloropropyl) nonylamide (8 millimoles (mmole)) was mixed with 10 milliliters (ml) of acetonitrile. To this mixture was slowly added 4 equivalents (4.7 g) of 40% potassium fluoride on alumina. This mixture was stirred mechanically until completion of the reaction. Completion of the reaction was followed by thin layer chromatography (TLC) on silica with an ethyl acetate eluent. The potassium fluoride on alumina reagent was filtered off through Celite and the acetonitrile was evaporated off. The resulting product was then vacuum distilled with a yield of about 31 percent.

EXAMPLE 6

The compound, 5-bromomethyl-2-phenyl-1,3-oxazoline, was synthesized from N-(2,3-dibromopropyl)benzamide following the procedure of example 2. The crude product was initially obtained as an oil. The compound was purified by dissolving in hexanes and decanting away the insoluble impurities. The hexanes solution was then slowly cooled to −50° C. which gave a 76% yield of the white crystalline product having a melting point of 31°–32° C. FTIR, HNMR and CNMR-DEPT indicated the presence of the compound, 5-bromomethyl-2-phenyl-1,3-oxazoline.

EXAMPLE 7

The compound, 5-methylene-2-phenyl-1,3-oxazine, was synthesized from one equivalent of benzamide, one equivalent of 3-chloro-2-choroethyl-1-propene, and six equivalents of potassium fluoride on alumina following the procedure of example 2. After filtration and evaporation of the acetonitrile, an oil was obtained which was taken up in cyclohexane to separate the product from the remaining benzamide. Evaporation of the solvent gave a 25% yield of a colorless oil. FTIR and HNMR indicated the presence of the compound, 5-methylene-2-phenyl-1,3-oxazine.

EXAMPLE 8

Preparation of 1,4-bis(1,3-oxazoline)-2-phenylene was as follows. N,N'-bis(2-chloroethyl)-1,4-terephthalamide (8 mmole) was mixed with 80 ml of acetonitrile. To this mixture was added 10 equivalents (11.5 g) of 40% potassium fluoride on alumina. This mixture was stirred mechanically for about 24 hours. The resultant slurry was then placed in a Soxhlet extractor and extracted with acetonitrile for one week. Evaporation of the solvent gave 1.30 g of pure product, a yield of about 87 percent.

EXAMPLE 9

Preparation of 1,4-bis(1,3-oxazine)-2-phenylene was as follows. N,N'-bis(2-chloropropyl)-1,4-terephthalamide (1.6 mmole) was mixed with 10 ml of acetonitrile. To this mixture was added 16 equivalents (3.5 g) of 40% potassium fluoride on alumina. This mixture was stirred mechanically for about 48 hours. The resultant slurry was then rinsed with 200 ml of acetonitrile. Evaporation of the solvent gave 0.32 g of pure product, a yield of about 79 percent.

EXAMPLE 10

Preparation of 4,4-dimethyl-2-vinyl-1,3-oxazoline was as follows. To 3 ml of Sulfolane was added 1 g (6 mmole) of N-(1-chloro-t-butyl)acrylamide and 4 equivalents (3.6 g) of 40% potassium fluoride on alumina. This mixture was stirred mechanically for about 10 hours. The product was then distilled at 50° C. under a vacuum of 30 mm Hg to give 0.11 g, a yield of about 14 percent.

Although the present invention has been described with reference to specific details, it is not intended that such details should be regarded as limitations upon the scope of the invention, except as and to the extent that they are included in the accompanying claims.

What is claimed is:

1. A process of preparing an oxazoline or oxazine compound of the formula

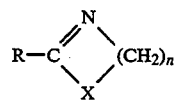

wherein X is selected from the group consisting of oxygen, R is selected from the group consisting of $C_{1-10}$ alkyl, $C_{1-10}$ fluoroalkyl, aryl and substituted-aryl, and n is 2 or 3, comprising ring-closing a compound of the formula

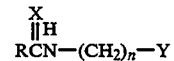

wherein X is selected from the group consisting of oxygen and sulfur, R is selected from the group consisting of $C_{1-10}$ alkyl, $C_{1-10}$ fluoroalkyl, aryl and substituted-aryl, n is 2 or 3, and Y is a bromine or chlorine atom, in the presence of a reagent consisting essentially of a fluoride salt selected from the group consisting of lithium fluoride, sodium fluoride, potassium fluoride, cesium chloride, and tetra-(lower alkyl)-ammonium fluorides supported on an inorganic solid substrate.

2. The process of claim 1 wherein the inorganic solid substrate is selected from the group consisting of alumina, silica gel, magnesium oxide, montmorillonite, and diatomaceous earth.

3. The process of claim 1 wherein the basic reagent consists essentially of potassium fluoride on an inorganic solid substrate of alumina.

4. In a process of preparing an oxazoline or oxazine compound by ring closure of one or more precursor materials, the improvement wherein said ring closure is conducted in the presence of a reagent consisting essentially of a fluoride salt selected from the group consisting of lithium fluoride, sodium fluoride, potassium fluoride, cesium chloride, and tetra-(lower alkyl)-ammonium fluorides supported on an inorganic solid substrate.

5. The process of claim 4 wherein the inorganic solid substrate is selected from the group consisting of alumina, silica gel, magnesium oxide, montmorillonite, and diatomaceous earth.

6. The process of claim 4 wherein the basic reagent consists essentially of potassium fluoride on an inorganic solid substrate of alumina.

* * * * *